(12) United States Patent
Sigfrid

(10) Patent No.: US 8,235,970 B2
(45) Date of Patent: Aug. 7, 2012

(54) DEVICE AFFIXING TUBES TO A CANNULA

(75) Inventor: Tracy Sigfrid, Coon Rapids, MN (US)

(73) Assignee: Tracy D. Sigfrid, Minneapolis, MN (US)

( * ) Notice: Subject to any disclaimer, the term of this patent is extended or adjusted under 35 U.S.C. 154(b) by 71 days.

(21) Appl. No.: 12/321,695

(22) Filed: Jan. 22, 2009

(65) Prior Publication Data

US 2009/0192497 A1 Jul. 30, 2009

Related U.S. Application Data

(60) Provisional application No. 61/011,725, filed on Jan. 22, 2008.

(51) Int. Cl.
*A61M 25/16* (2006.01)

(52) U.S. Cl. ........ 604/533; 604/534; 604/535; 128/912; 128/DIG. 26

(58) Field of Classification Search ............... 604/264, 604/523, 533, 534, 535, 538, 284, 77, 178, 604/180, 905; 128/207.14, 912, DIG. 26
See application file for complete search history.

(56) References Cited

U.S. PATENT DOCUMENTS

| | | | | |
|---|---|---|---|---|
| 4,057,066 A | * | 11/1977 | Taylor | 604/180 |
| 4,326,515 A | * | 4/1982 | Shaffer et al. | 128/207.17 |
| 4,460,356 A | * | 7/1984 | Moseley | 604/180 |
| 5,699,787 A | * | 12/1997 | Thompson | 128/200.26 |
| 6,612,309 B1 | * | 9/2003 | Ancona | 128/207.17 |

* cited by examiner

*Primary Examiner* — Bhisma Mehta
(74) *Attorney, Agent, or Firm* — Angenehm Law Firm; N. Paul Friederichs

(57) ABSTRACT

A medical device including: a cannula, a first tube joined to the cannula; a second tube joined to the cannula; and a unitary fastener secured to the first tube, cannula and second tube, the fastener being subject to opposing forces from the first and second tubes.

20 Claims, 9 Drawing Sheets

US 8,235,970 B2

DEVICE AFFIXING TUBES TO A CANNULA

FIELD OF THE INVENTION

The present invention relates to medical cannulas and more particularly device for affixing tubes to a cannula, claiming priority from U.S. Provisional Application 61/011,725, filed Jan. 22, 2008.

BACKGROUND OF THE INVENTION

Patients on various life support have tubes placed into the lungs or stomach. Such tubes are affixed to a cannula, a form of junction box a few inches from the mouth of the patient. Tubes can be replaced, added and removed from the cannula as medical treatment needs are modified.

Cannulas, however, have a known problem. The tubes are positioned into portions of the human body known to issue moisture. The moisture in turn pools and collects in and around junctures between the tubes and cannula. The moisture weakens or degrades the manners of affixing the tubes to the cannula, which are typically tape wrapped circularly about the junction, forming a poor seal. As moisture pools in the junction, it attacks the underside of the tape causing it to separate from the tube and/or cannula. The moisture continues to pool until it separates enough of the tape from the tube/cannula to allow escape of the fluids. At this point, the tape is generally too degraded to provide the necessary hold. A shift of the patient, causes tubes to become dislodged, depriving the patient of needed medical care.

Hospital procedures have been developed to overcome this problem, including frequent examination of the tubes and cannula to assure connection. This examination has led to higher labor costs than necessary if the tubes would remain fixed until medical personal wanted them removed. Often the equipment needs to be replaced prematurely due to separation of components, causing higher material costs.

What is needed is a device that secures to the tube and the cannula. Ideally, the fastener, preferably tape, receives opposing forces from the cannula and at least one other tube, while leaving at least a portion of the junction open to release fluid. For instance, a length of tape is joined to a tube and cannula, but desirably is also joined to at least one other tube positioned in a direction opposing the first tube. More preferably, one length of tape secures three tubes and the cannula in opposing directions.

SUMMARY OF THE INVENTION

The present invention is a fastener that secures a tube to a cannula. The fastener, preferably tape, ideally receives opposing forces from the cannula and at least one other tube, while leaving at least a portion of the junction open to release fluid. For instance, a length of tape is joined to a tube and cannula, but is also joined to at least one other tube positioned in a direction opposing the first tube. In its preferred form, the fastener, perhaps length of tape, secures three tubes in opposing directions across the cannula.

In a preferred embodiment the medical device has a cannula. A first tube and a second tube are joined to the cannula. A unitary fastener is secured to the first tube, cannula and second tube such that the fastener is subject to opposing forces from the first and second tubes across the cannula.

Advantageously, the fastener may be positioned to allow a path of water vapor emitted by a patient.

As a further advantage, the fastener is not subject to weakening or degradation from interaction with water vapors of a patient.

As still yet another advantage, tubes remain secured to the cannula and reduce the human labor and materials needed to maintain the medical apparatus.

Also advantageously, the present invention can be extended to secure a number of tubes.

These and other advantages will be understood through reading the below detailed description of the preferred embodiment with reference to the drawings.

IN THE FIGURES

Figure 1:
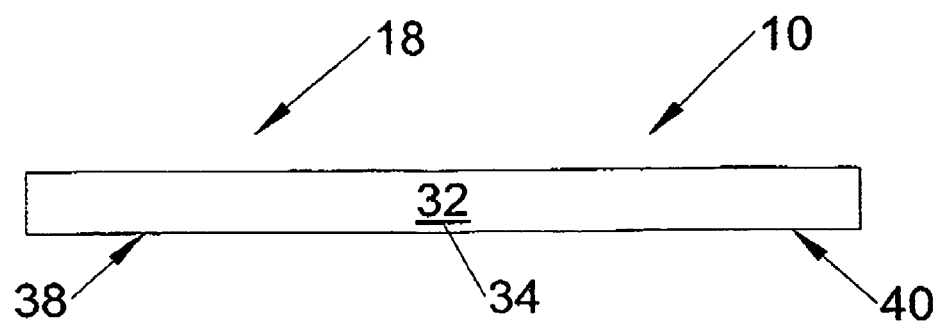
FIG. 1 is a top plan view of the preferred fastener of the present invention.
Figure 2:
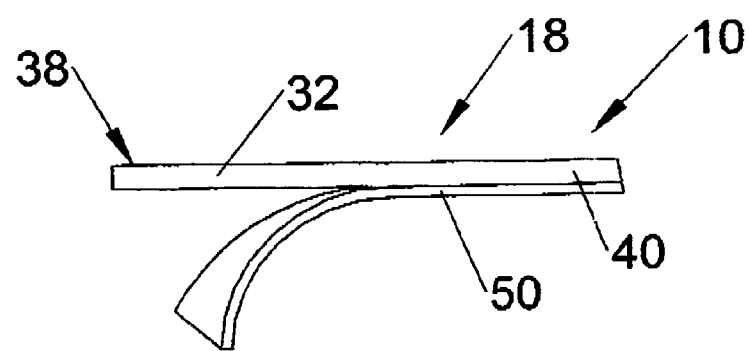
FIG. 2 is a perspective view of the preferred fastener of the present invention, showing a cover being pealed from the fastener.
Figure 3:
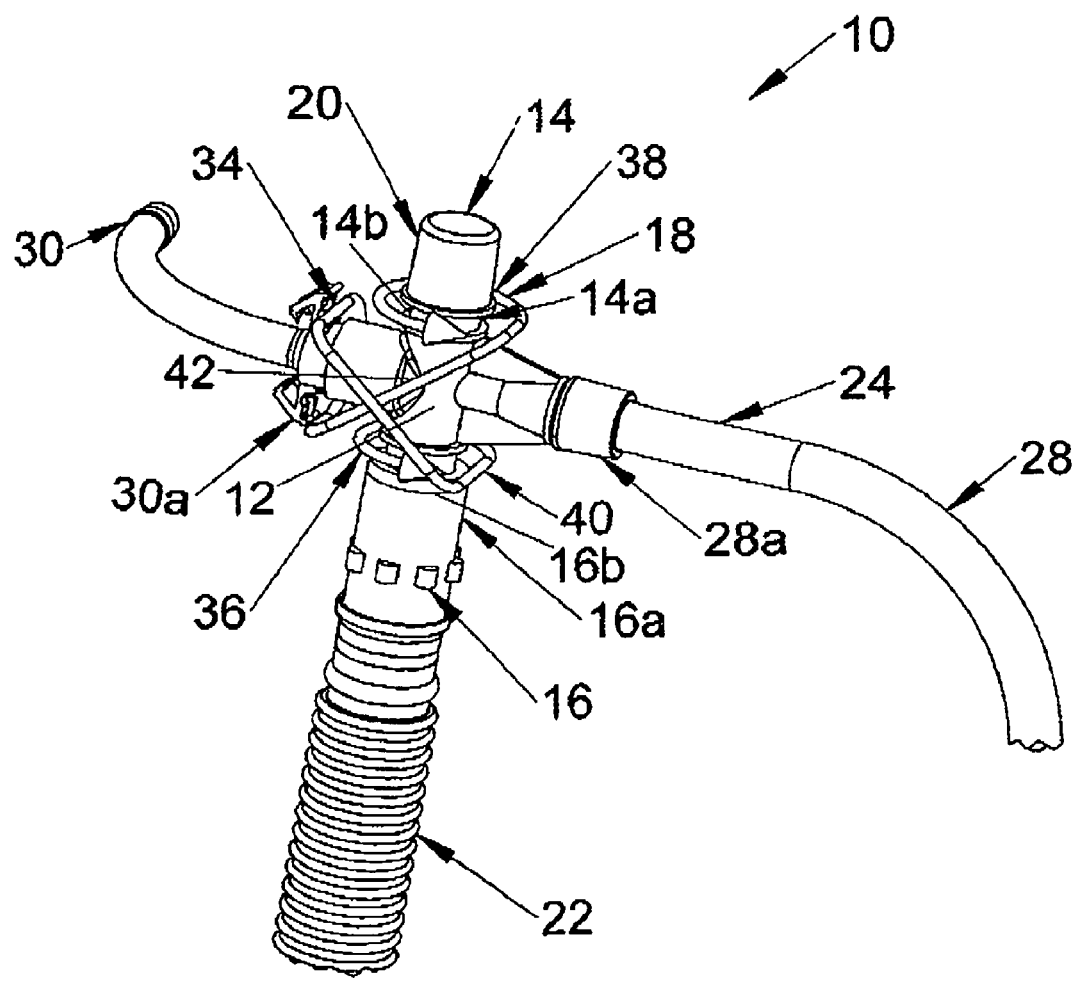
FIG. 3 is a perspective view showing the preferred fastener securing the preferred number of tubes to a cannula.
Figure 3A:
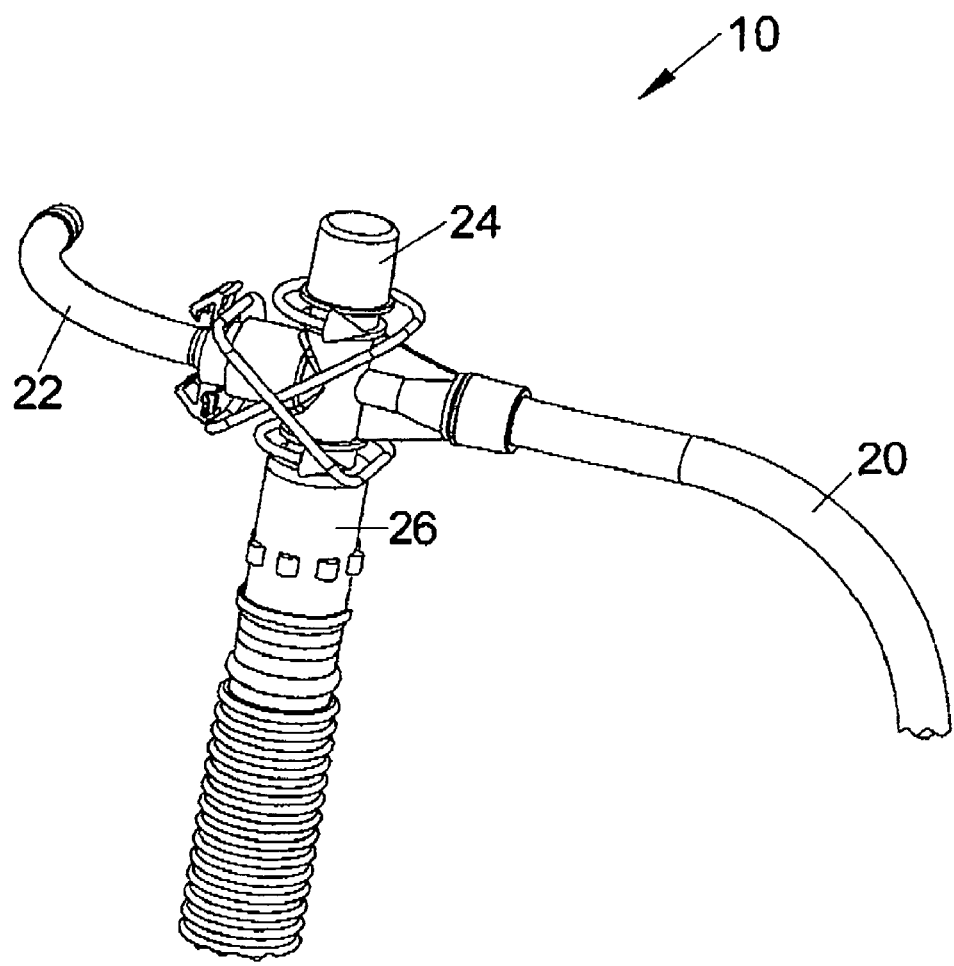
FIG. 3a is the perspective view of FIG. 3, showing an alternative embodiment and in particular the naming and numbering of the tubes 20, 22, 24, and 26 as not being limiting.
Figure 3B:
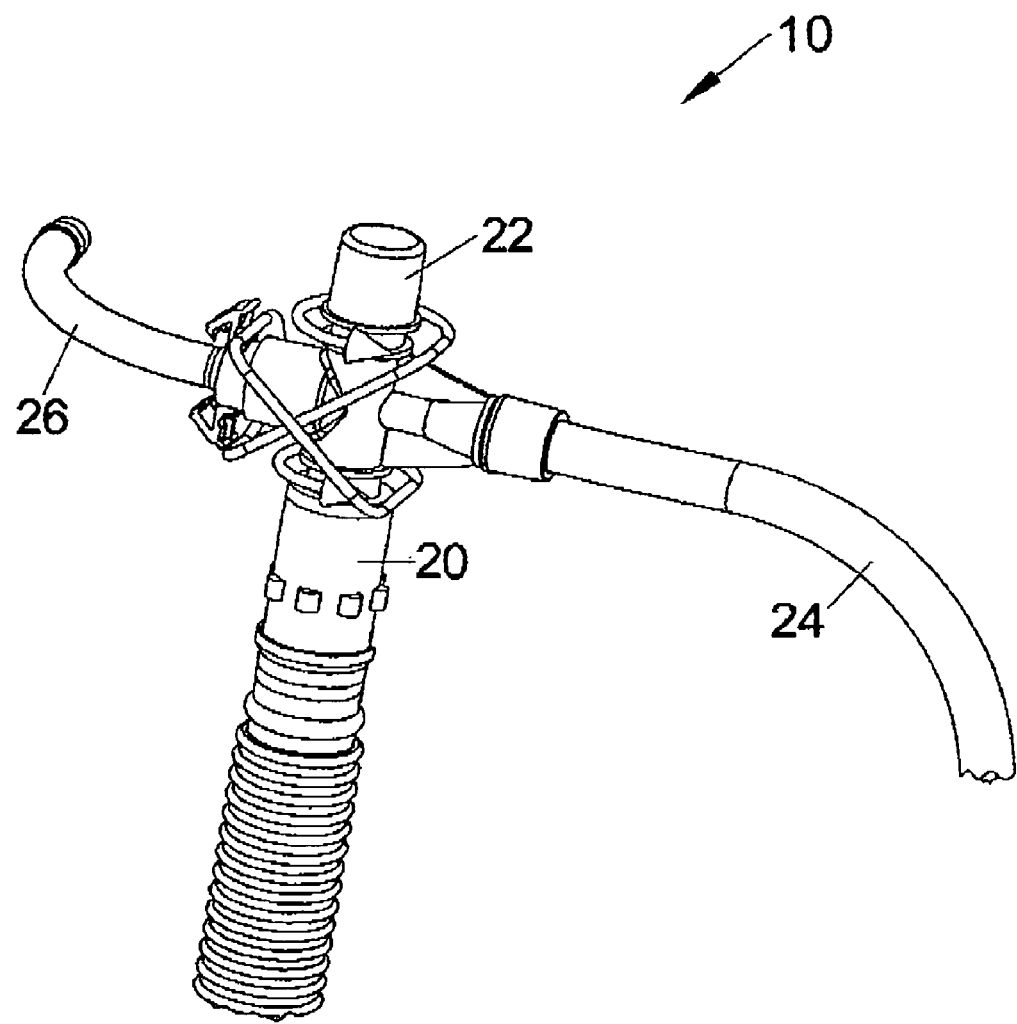
FIG. 3b is the perspective view of FIG. 3, showing an alternative embodiment and in particular the naming and numbering of the tubes 20, 22, 24, and 26 as not being limiting.
Figure 3C:
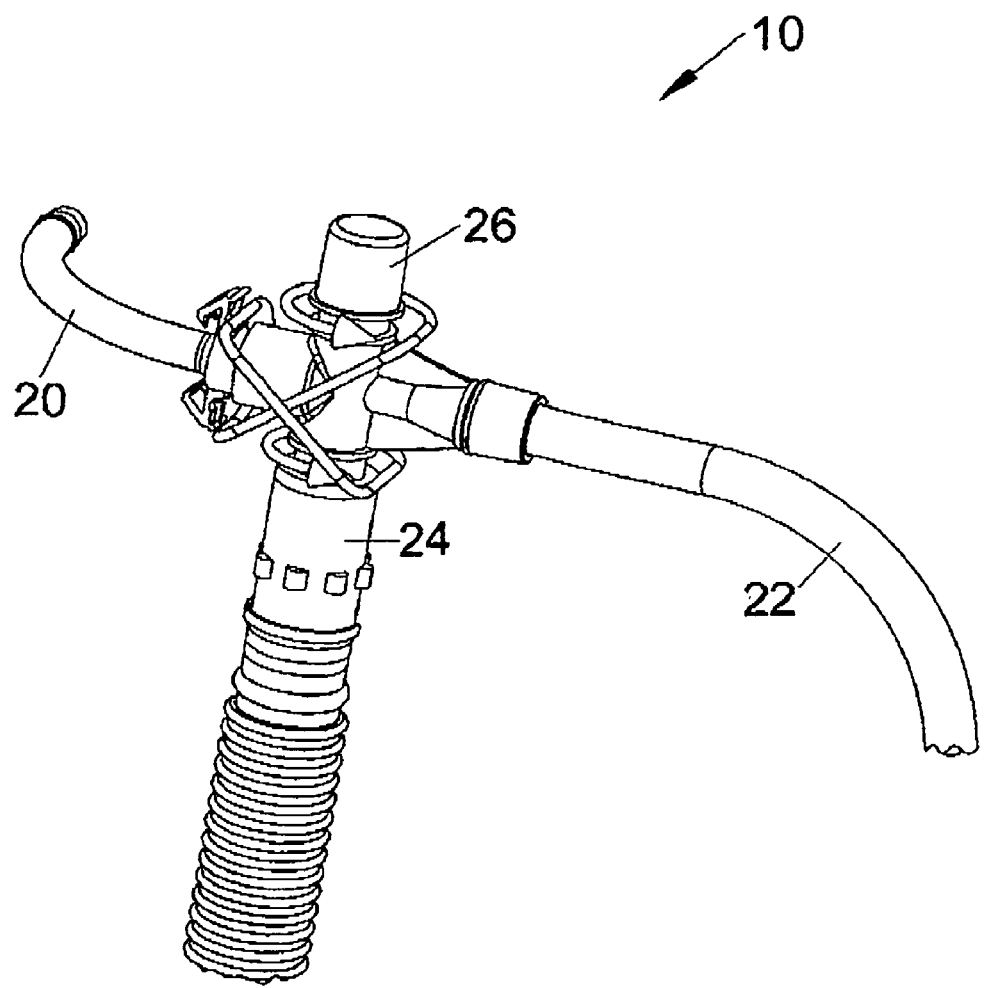
FIG. 3c is the perspective view of FIG. 3, showing an alternative embodiment and in particular the naming and numbering of the tubes 20, 22, 24, and 26 as not being limiting.
Figure 3D:
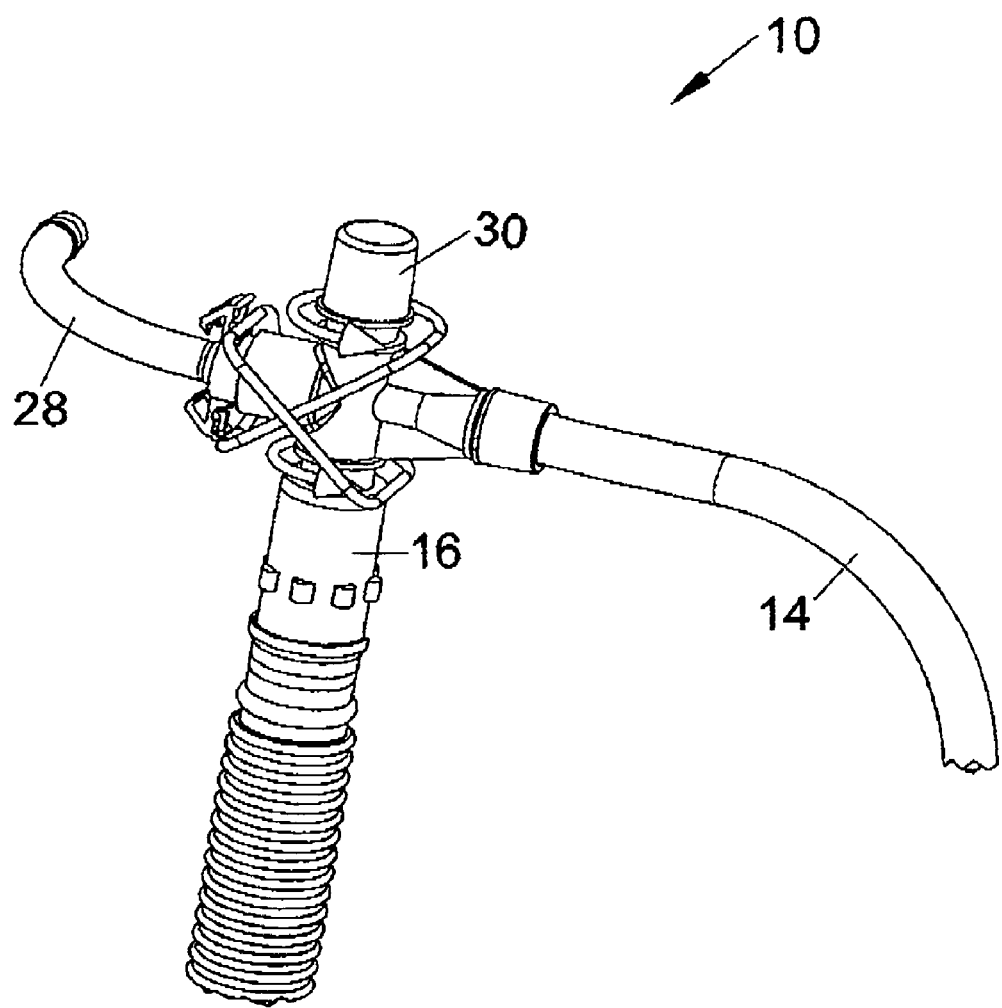
FIG. 3d is the perspective view of FIG. 3, showing an alternative embodiment and in particular the naming and numbering of the tubes 14, 16, 28, and 30 as not being limiting.
Figure 3E:
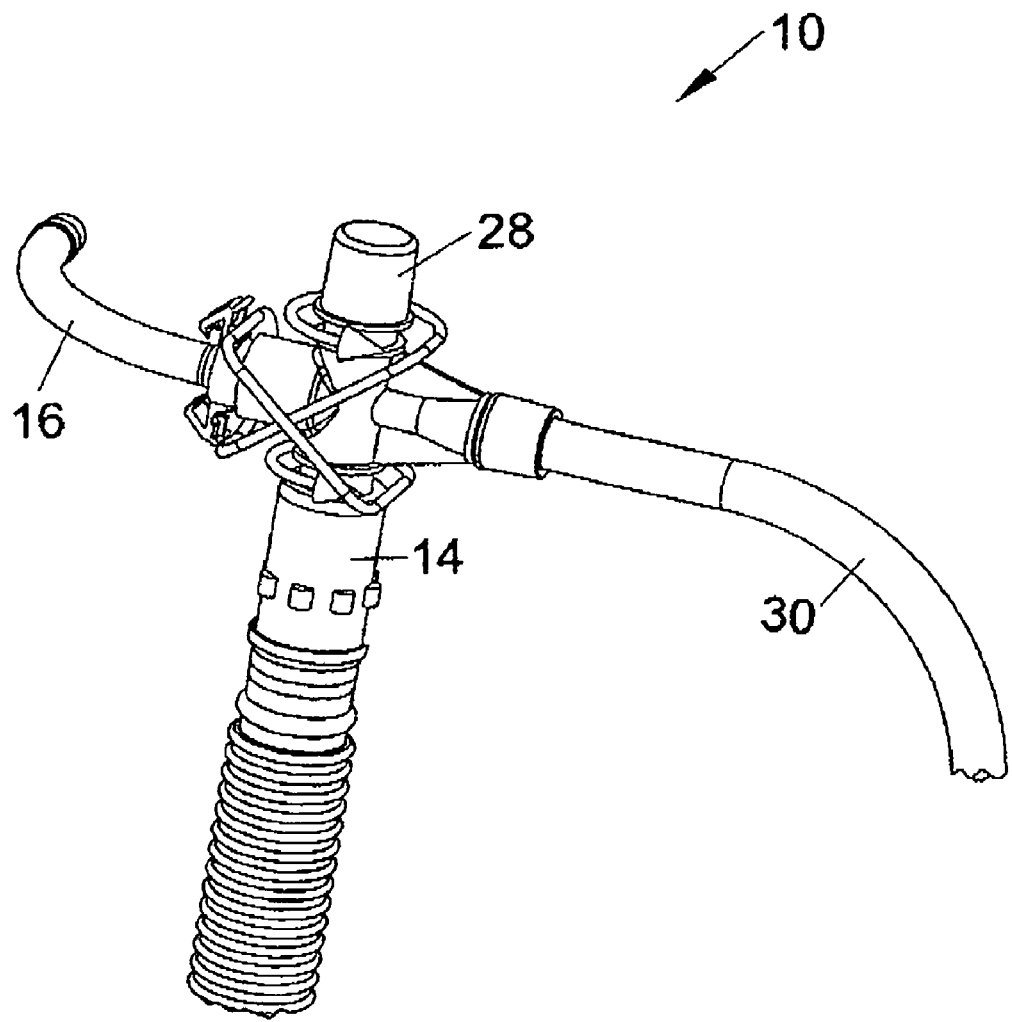
FIG. 3e is the perspective view of FIG. 3, showing an alternative embodiment and in particular the naming and numbering of the tubes 14, 16, 28, and 30 as not being limiting.
Figure 3F:
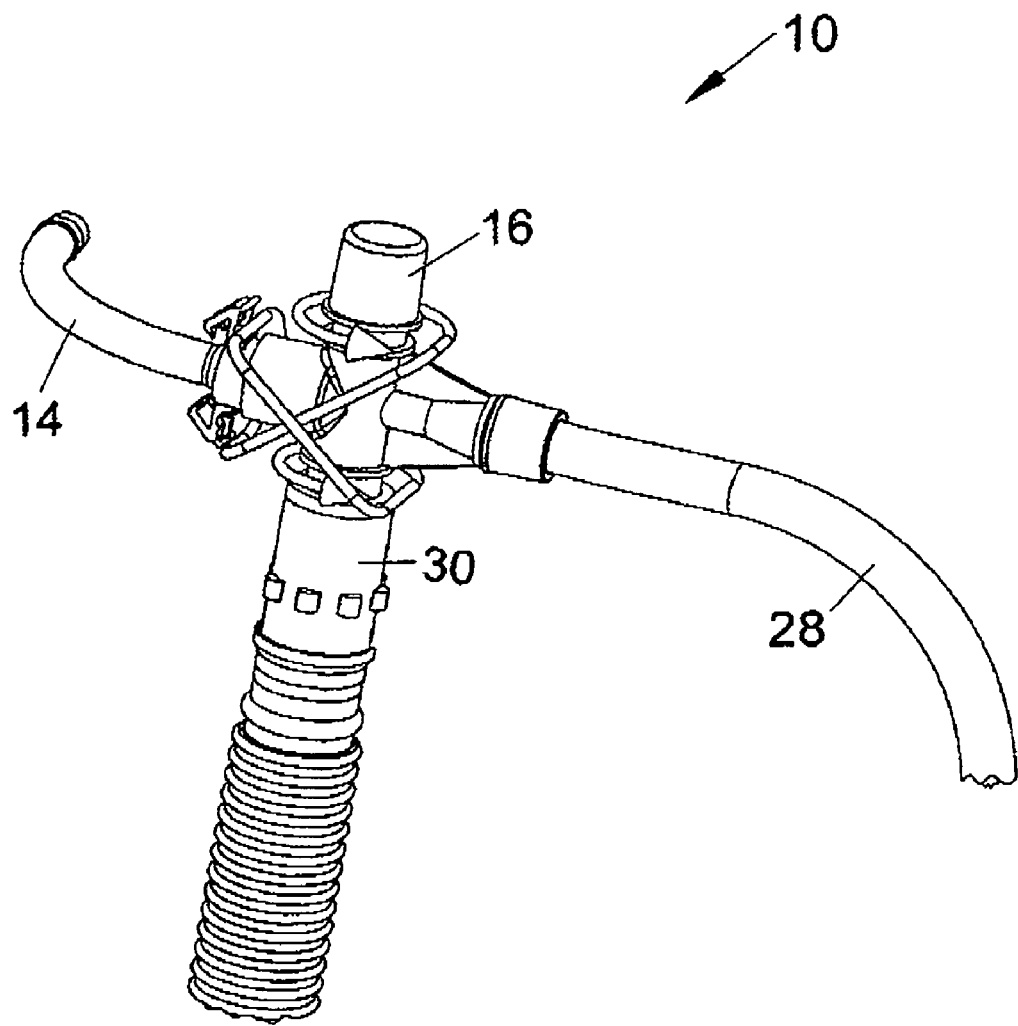
Figure 3G:
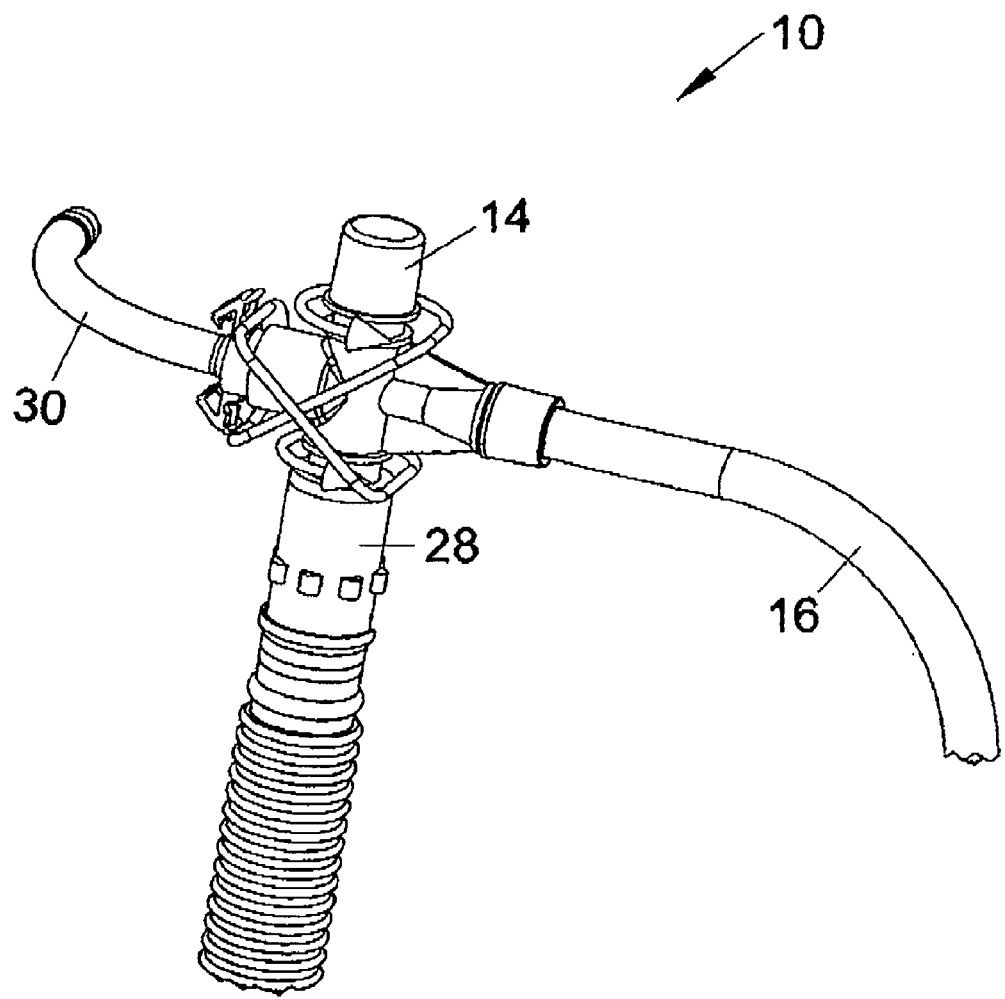

FIG. 3f is the perspective view of FIG. 3, showing an alternative embodiment and in particular the naming and numbering of the tubes 14, 16, 28, and 30 as not being limiting; and FIG. 3g is the perspective view of FIG. 3, showing an alternative embodiment and in particular the naming and numbering of the tubes 14, 16, 28, and 30 as not being limiting.

DETAILED DESCRIPTION OF THE INVENTION

The present invention is a medical device 10 and may include a cannula 12, first tube 14, second tube 16 and a unitary fastener 18. The first tube 14 may be selectively joined to the cannula 12 at a junction 14a. The first tube 14 may be a proximal tube 20, a distal tube 22, a right tube 24 or a left tube 26.

The second tube 16 may also be selectively joined to the cannula 12 at a junction 16a. The second tube 16 may be a proximal tube 20, a distal tube 22, a right tube 24 or a left tube 26 and is positioned in a direction opposing the first tube 14. That is, the second tube may be a member selected from the group including proximal tube 20, a distal tube 22, a right tube 24 or a left tube 26 not being the same member as the first tube 14. The ends 14b, 16b of the first and second tubes 14, 16, as shown in FIG. 3, join the respective tubes 14, 16 to the cannula 12 while the end 16b of the second tube 16 is fixed in a position relative to the cannula 12 in a direction opposing the end 14b of the first tube 14. The end 14b of the first tube 14 is in a fixed position relative to the cannula 12. "Opposing" is intended to carry the meaning biased in an angular, 75 degrees through 285 degrees, fashion, ex., differing sides of a cannula 12.

Third and fourth tubes 28, 30 may also be selectively joined to the cannula 12 at junctions 28a, 30a respectively and may be a proximal tube 20, a distal tube 22, a right tube 24 or a left tube 26. All such tubes, 14, 16, 28, 30 may be joined to the cannula 12 in an opposing manner with respect to each other.

A unitary fastener 18, e.g., one piece, may secure to the first tube 14, cannula 12 and the second tube 16, such that the fastener 18 preferably is subject to opposing forces the first and second tubes 14, 16 across the cannula 12. Desirably, the unitary fastener 18 is non-stretchable, where non-stretchable is defined to be any amount of stretch less than is necessary to allow the first tube 14 or second 16 to disengage from the cannula 12. The fastener 18 in its preferred form is tape 32, preferably medical grade, such as product 1525L (Single coated medical tape) sold by Minnesota Mining and Manufacturing, Inc. In a preferred mode, the unitary fastener 18 secures the first, second and third tubes 14, 16, 28 in an opposing manner across the cannula 12. That is, the unitary fastener 18 secures three tubes to the cannula 12 in opposing directions.

A segment of medical tape 32 desirably has a length, perhaps six or more inches, greater than its width, perhaps one-half or greater inches. Each end 38, 40 of the tape 32 may be wrapped about the first and second tubes 14, 16, leaving at least a position of junctions 14a and 16a exposed to release water vapor. The tape 32 may also have a midpoint 34 along the length. Where three tubes are joined to the cannula 12, the midpoint 34 may be secured to the middle tube, which may be the proximal tube 20.

The mid-point 34 desirably is disposed about a first tube, 14, perhaps the proximal tube 20, leaving at least a position of junction 14a exposed to release water vapor. The tape 32 may be positioned in an X configuration 36 across the cannula 12, and each end 38, 40 of the tape 32 wrapped, perhaps circularly, about second and third tubes 16, 28, which may be the right and left tubes 24, 26 respectively. The X configuration 36 may be positioned over a center 42 of the cannula 12. The ends 38, 40 may be adhered to tubes 16, 28 in a manner that leaves at least a position of junctions 16a and 28a exposed to release water vapor.

The tape 32 is non-stretch, where non-stretch is defined to be any amount less than the stretch necessary to allow dislodging any of the tubes 14, 16, 28, 30 from the cannula 12. Preferably, the tape 32 is sufficiently clear such that a viewer may visually examine moisture migration, if any, under the tape 32. The preferred embodiment of the present invention has the length of tape 32, clear, securing three tubes and the cannula 12 in opposing directions.

The present invention has been described disclosing the best mode of making and using the present invention. Changes may be made in form and in substance without departing from the spirit and scope of the present invention. For instance a cover, such as cover 50 may maintain the integrity of an adhesive until use.

I claim:

1. A medical device, comprising:
   a cannula;
   a first tube joined to the cannula;
   a second tube joined to the cannula; and
   a unitary fastener joined and secured to an end of the first tube, the cannula and an end of the second tube, the fastener being subject to opposing forces from the first and second tubes across the cannula and the ends of the first and second tubes joining the respective tubes to the cannula while the end of the second tube is fixed in a position angularly biased with respect to the end of the first tube at an angle between 75 degrees through 285 degrees and the end of the first tube being in a fixed position relative to the cannula.

2. The device of claim 1 wherein the fastener is tape.

3. The device of claim 1 wherein the first tube is a member selected from the group consisting of a proximal tube, a distal tube, a right tube and a left tube.

4. The device of claim 3 wherein the second tube is a member selected from the group consisting of a proximal tube, a distal tube, a right tube and a left tube, but the second tube not being the same member as the first tube.

5. The device of claim 4 wherein the unitary fastener joined to the first and second tubes and cannula, is also joined to a third tube positioned in a direction opposing the first and second tubes.

6. The device of claim 1 wherein the unitary fastener secures three tubes in opposing directions, such three tubes including the first tube and second tube.

7. The device of claim 6 wherein the third tube is a member selected from the group consisting of a proximal tube, a distal tube, a right tube and a left tube.

8. The device of claim 1 further wherein the unitary fastener is a segment of tape having a length greater than its width and having a midpoint along the length disposed between opposing ends of the tape, the midpoint being disposed about a proximal tube adjacent a juncture of the proximal tube and cannula, the tape wrapped in an "X" configuration across the cannula, one end of the tape wrapped about the first tube and another end of the tape wrapped about the second tube and the first and second tubes being right and left tubes respectively.

9. The device of claim 8 wherein the tape has a length of at least six inches.

10. The device of claim 8 wherein the tape has a width of at least ½ inches.

11. The device of claim 8 wherein the tape forms an "X" configuration with the "X" centered over the cannula.

12. The device of claim 1 wherein the unitary fastener is a segment of medical tape having a length greater than its width, the tape wrapped about the first and second tubes.

13. The device of claim 12 wherein the tape is non-stretchable to preclude dislodging of the first and second tubes from the cannula.

14. The device of claim 12 wherein the tape has a midpoint along the length.

15. The device of claim 14 wherein the mid-point is disposed about a proximal tube adjacent a juncture of the proximal tube and cannula.

16. The device of claim 15 wherein the tape is wrapped in an "X" configuration across the cannula.

17. The device of claim 12 wherein the tape has a length of at least 6 inches.

18. The device of claim 12 wherein the tape has a width of at least ½ inches.

19. The device of claim 12 wherein the tape is clear.

20. The device of claim 12 wherein the length of tape secures three tubes and the cannula with at least two of the tubes being oriented in opposing directions, said three tubes being the first tube, the second tube and a proximal tube.

* * * * *